US006258231B1

United States Patent
Easter et al.

(10) Patent No.: US 6,258,231 B1
(45) Date of Patent: Jul. 10, 2001

(54) CHEMICAL MECHANICAL POLISHING ENDPOINT APPARATUS USING COMPONENT ACTIVITY IN EFFLUENT SLURRY

(75) Inventors: William Graham Easter; Sudhanshu Misra; Pradip Kumar Roy; Susan Clay Vitkavage, all of Orlando, FL (US)

(73) Assignee: Agere Systems Guardian Corp., Allentown, PA (US)

( * ) Notice: Subject to any disclaimer, the term of this patent is extended or adjusted under 35 U.S.C. 154(b) by 0 days.

(21) Appl. No.: 09/432,721

(22) Filed: Nov. 1, 1999

(51) Int. Cl.[7] ................................................ G01N 27/406
(52) U.S. Cl. .................. 204/421; 204/422; 205/783.5; 216/86; 216/89; 451/8; 451/41
(58) Field of Search ........................... 204/421, 422, 204/400; 216/86, 89; 451/8, 41; 438/10, 17; 205/775, 791, 790.5, 783.5

(56) References Cited

U.S. PATENT DOCUMENTS

| | | | |
|---|---|---|---|
| 4,645,571 | * | 2/1987 | Dubreuil et al. ................. 204/422 |
| 4,917,775 | * | 4/1990 | Rantapuska ....................... 204/402 |
| 5,266,152 | * | 11/1993 | Iwasaki et al. ................... 216/86 |
| 5,277,781 | * | 1/1994 | Matsubara et al. ............... 204/421 |
| 5,637,185 | * | 6/1997 | Murarka et al. .................. 216/86 |
| 5,846,398 | * | 12/1998 | Carpio ............................... 205/775 |

OTHER PUBLICATIONS

Kalkarai et al. "Stability of Solid Electrolyte Concentration Sensors for Automatic Oxgen Control in Liquid Copper", J. Institute Metals, v. 99, pp. 15–18.*

* cited by examiner

Primary Examiner—Robert J. Warden, Sr.
Assistant Examiner—Kaj K. Olsen
(74) Attorney, Agent, or Firm—Christie, Parker & Hale, LLP (57) ABSTRACT

An apparatus for determining the endpoint in a chemical mechanical polishing operation used for polishing a metal-containing material includes an electrochemical cell and an electronic circuit. An acidic polishing slurry is used to oxidize the metal and the oxidized metal is included in an effluent slurry stream, a sample of which is provided to the apparatus. The apparatus includes a liquid-phase working electrode, a reference electrode and a solid electrolyte which allows for the interchange of ions between the electrodes. An electronic circuit is coupled to the electrode for monitoring the component activity of the effluent slurry stream by measuring the electric potential across the electrodes. When the measured electric potential changes, indicating a change in the composition of the effluent slurry, endpoint is indicated.

19 Claims, 3 Drawing Sheets

CHEMICAL MECHANICAL POLISHING ENDPOINT APPARATUS USING COMPONENT ACTIVITY IN EFFLUENT SLURRY

FIELD OF THE INVENTION

The present invention relates generally to chemical mechanical polishing of substrates, and more particularly to the detection of a polishing endpoint by monitoring the component activity in effluent slurry of the polishing operation using an apparatus including an electrochemical cell.

BACKGROUND OF THE INVENTION

Chemical mechanical polishing (CMP) is one method of providing a planarized substrate surface. Such substrates are used in the manufacture of integrated circuit devices. CMP may be used to planarize raw substrates or to completely or partially remove a bulk deposited layer, but is more commonly used to planarize a surface by partially removing layers which have been deposited over non-planar features formed in, or on, a subjacent layer. A typical CMP apparatus employs a rotating polishing surface, such as a consumable polishing pad, against which the surface of the substrate being polished, is placed. The CMP apparatus also includes a carrier which secures the substrate in a desired position with respect to the pad. The carrier includes means for providing a force to keep the substrate in contact with the pad, and may also include means for rotating, vibrating, or oscillating the substrate. During polishing, a slurry having both chemical and abrasive agents is supplied to the interface between the substrate and the pad to enchance the rate at which material is removed from the substrate. The chemical agents included in the slurry are generally chosen to be reactive towards the material being removed by polishing. The effluent slurry therefore includes products containing components of the material removed by polishing.

One problem associated with CMP is endpoint detection. Endpoint may be defined as the point at which the desired polishing operation is completed. When "endpoint" is attained, a number of different actions may be taken in response. For example, the entire polishing process may be terminated when endpoint is attained or the polishing conditions may be changed as the polishing process continues with another polishing operation, to polish an underlying film. It can be seen that a substrate containing a stack of films to be polished, may include a number of discrete polishing operations, each of which includes an associated "endpoint".

Depending on the chemical mechanical polishing operation being performed, "endpoint" may signify different events. For example, when polishing a raw substrate, "endpoint" may be attained when a certain predetermined substrate thickness has been removed. The same is true for a layer or film which is being partially removed. When a film is being completely removed from a substrate, "endpoint" is attained upon complete removal of the film. When CMP is used to planarize a substrate by removing portions of a film which extend above underlying features, "endpoint" is attained when the surface is essentially planar. Generally speaking, an endpoint condition is attained after a predictable amount of material has been removed from the surface. It is therefore necessary to accurately detect when endpoint is reached so that the polishing operation may be quickly terminated or otherwise adjusted at that point. Because the substrate is polished face-down and the polishing surface is generally contiguous with the polishing pad, a process monitor cannot easily be used to view the progress of the polishing operation, especially by directly monitoring the surface being polished. As such, it is difficult to attempt to use such a monitor to determine the polishing "endpoint."

Variations in the polishing conditions also impede an accurate determination of the polishing endpoint. For example, variations in the slurry composition and flow rate, pad condition, relative speed between the pad and the substrate, the material being polished, and the load of the substrate on the pad, cause variations in the material removal rate. These variations in the material removal rate cause variations in the time needed to reach the polishing endpoint. Therefore, the polishing endpoint cannot reliably be estimated merely as a function of polishing time.

A common object of CMP is to planarize a substrate surface using damascene technology. In damascene technology, trenches, grooves or other openings may be formed within a subjacent layer such as a dielectric film formed over a substrate. Next, a bulk deposited layer, generally a conductive film such as metal, is formed over the upper surface of the subjacent layer and within the openings which extend down into the subjacent layer. One aspect of CMP is to remove the bulk of the deposited conductive layer from over the plane formed by the upper surface of the subjacent layer, leaving areas of the conductive layer only in the openings formed within the subjacent layer. In this manner, a wiring pattern is produced. It can be understood that it is desirable to terminate the polishing operation when endpoint is attained, i.e. when the bulk of the deposited conductive film is removed from over the plane formed by the upper surface of the subjacent layer, but remains within the openings so that the remaining portions of the conductive film form a substantially planar surface with the upper surface of the subjacent layer.

One general approach to predicting the polishing endpoint is to remove the substrate from the polishing apparatus and measure the thickness of the substrate or the film being removed by polishing. By periodically removing the substrate from the polishing apparatus and measuring its thickness, the quantity of material being removed from the substrate may be determined. As such, a linear approximation of the material removal rate may be used to determine the polishing endpoint. This technique is time consuming, however, and does not account for sudden changes in the removal rate that may occur between measurement intervals, or for other variations in the material removal rate as discussed above.

Several other non-invasive techniques for endpoint detection are known. These techniques generally fall into two categories: those which require access to the surface of the substrate being polished, and those which determine the polishing endpoint by determining changes in the operating conditions of the polishing apparatus.

Techniques included within the first category typically require real-time access to at least a portion of the substrate surface being polished, such as by sliding a portion of the substrate over the edge of the polishing pad and simultaneously analyzing the exposed portion of the substrate. For example, where polishing is used to remove the bulk of a metal film, and to form metal lines embedded within trenches formed in a subjacent dielectric layer as in the planarization example discussed above, the overall or composite reflectivity of the surface being polished changes as the bulk metal film is removed and the dielectric layer is exposed. By monitoring the reflectivity of the polished surface or the wavelength of light reflected from the surface, the polishing endpoint can be detected as the reflectivity changes when the dielectric layer is exposed. However, this technique does not provide a way of determining the polishing endpoint unless an underlying layer such as the dielectric is exposed during polishing and has a reflectivity which varies from that of the film being removed by polishing. Additionally, it is somewhat erratic in predicting the polishing endpoint unless all of the underlying surface of a different reflectivity, is simultaneously exposed. Furthermore, the detection apparatus is delicate and subject to frequent breakdown caused by the exposure of the measuring or detecting apparatus to the polishing slurry.

Another technique included within first category involves projecting a laser beam through an opening formed in the polishing pad, and onto the surface being polished. This technique is not favored because of the difficulty associated with projecting a laser through an opening which must be formed in an otherwise uninterrupted, rotating polishing pad. Additionally, the window, through which the laser beam is projected, must be kept clean. This is quite difficult to do, especially with some commonly used polishing slurries.

Techniques for determining the polishing endpoint included within the second category, monitor various operating conditions of the polishing apparatus and indicate an endpoint when one or more of the operating conditions abruptly changes. An example of such a condition is the coefficient of friction at the interface of the polishing pad and the substrate. When a metal layer is being polished to expose an underlying dielectric layer, for example, the coefficient of friction will change when the dielectric layer is exposed. As the coefficient of friction changes, the torque necessary to provide the desired polishing pad speed also changes. By monitoring this change such as by monitoring the polishing motor current, endpoint may be detected. However, the coefficient of friction is a function of the slurry composition, the pad condition, the load of the substrate on the pad, and the surface condition of the substrate. In addition, the pad condition and the slurry composition at the pad-substrate interface change as the substrate is being polished. Moreover, electrical noise may distort the characteristic being measured. Such effects may mask the exposure of the underlying dielectric layer (and removal of the bulk of the metal film), and may cause endpoint to be indicated at the incorrect time. Additionally, using this technique, the endpoint detection will work only if polishing is used to expose an underlying material having a frictional attribute different than that of the material being removed.

Another technique for determining endpoint included within the second category involves monitoring the current supplied to each of the polishing motors such as the motor which rotates the polishing pad or a motor which may be used to rotate the substrate being polished. Using this technique, a determination that endpoint has been achieved, may be made when a pre-determined total amperage is reached. Like the other techniques within the second category of endpointing techniques, this technique also does not directly monitor physical activity occurring on the surface being polished, during the polishing operation.

Therefore, none of the available endpointing techniques described above, detects endpoint by directly monitoring the amount of film being removed, or other physical changes occurring on the surface being polished, without interrupting the polishing process. As such, none of the known techniques for determining endpoint, do so by actually sampling the surface during the CMP operation, and detecting that the bulk of the film being polished, is physically removed from the surface. It can be understood, then, that such a method, and an apparatus for performing the same, are desirable in the art of CMP.

For the aspect of CMP directed to forming conductive lines within trenches or the like using damascene techniques, endpoint is achieved when the bulk of the conductive material is removed from over the upper surface of the subjacent layer, but remains within the trenches formed in the subjacent layer, to produce a planar surface. At this point, it is desirable to terminate the polishing process. Since the polishing slurry includes chemical components which are reactive towards the conductive material being polished, the effluent slurry includes components of the conductive material being removed by polishing. As such, when endpoint is achieved, the composition of the effluent slurry changes as the concentration of the conductive material within the effluent slurry, drops.

It can be seen that there is a need for an endpoint detection apparatus which detects endpoint at this point, in order to terminate or otherwise adjust the polishing operation to avoid further undesired polishing.

SUMMARY OF THE INVENTION

The present invention relates to an endpoint detection system for use in conjunction with a chemical mechanical polishing operation. A metal containing is film is polished using an acidic slurry. A sample of the effluent slurry is directed to a vessel in which an electrochemical cell is formed and in which the sample serves as a liquid phase working electrode within the electrochemical cell. The electrochemical cell includes a solid electrolyte solution chosen to allow for chemical interaction between the liquid phase working electrode and a reference electrode. Lead wires are placed in each electrode.

Half-cell reactions occur within the electrodes of the electrochemical cell, and the difference in chemical potential between the working electrode and the reference electrode causes the diffusion of ions across the electrolyte. At equilibrium, the chemical potential gradient is balanced by an electric potential gradient and is indicated by a stable open circuit electromotive force (emf) across the electrolyte. This emf, measured in volts or millivolts, is measured as a function of time using an electronic circuit coupled to the lead wires. A signal is developed reflecting the electric potential difference in time, and endpoint is detected responsive to changes in the measured electric potential signal. When endpoint is detected, the polishing operation may be terminated or otherwise adjusted.

DETAILED DESCRIPTION OF THE INVENTION

As discussed above, chemical mechanical polishing may be used for a wide range of polishing operations. One common example of such a polishing operation is the removal of a conductive film by means of polishing. The removal rate of the conductive film during a polishing operation depends on a number of factors such as the condition of the polishing pad, the composition and flow rate of the polishing slurry used, the power provided by the polishing motor, the film itself, the force applied to urge the polishing surface against the pad, the speed of rotation of the polishing pad, and the speed of rotation of the substrate being polished. Because a number of the preceding factors may change during a polishing operation, it is generally not advisable to attempt to terminate a polishing operation based simply upon polishing time.

The present invention is directed to detecting endpoint during the polishing of a metal-containing film. The metal-containing film may be a metal film commonly used as an interconnect material such as aluminum, copper, tungsten, or their alloys, or it may be a film commonly used as a barrier material such as tungsten silicide, titanium, titanium nitride, titanium silicide, tantalum, tantalum nitride, tantalum silicide, or other refractory metals. The film is removed by polishing. Endpoint is determined according to the present invention when the bulk of the metal-containing film, or the bulk of an individual metal-containing film within a stack of films, is substantially removed. The bulk, metal-containing film being endpointed may be formed over a planar substrate, or it may include portions additionally formed within openings formed in the underlying substrate.

Figure 1:
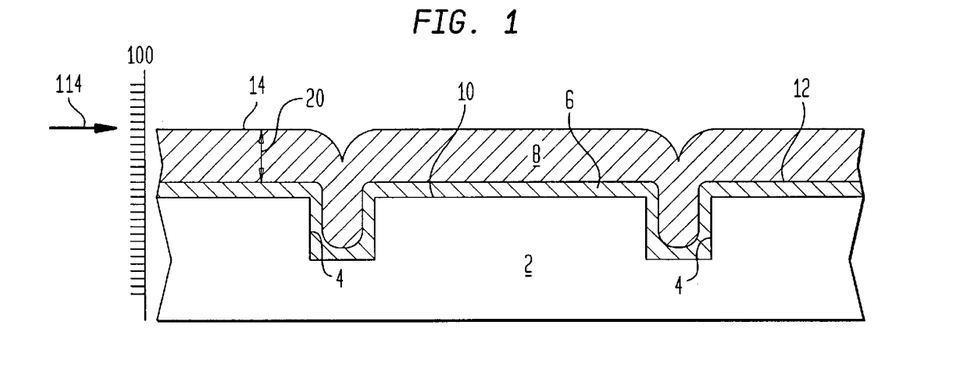
FIG. 1 is a cross-sectional view showing metal and barrier layer films included within trenches formed in the substrate to be polished.

A common application for chemical mechanical polishing is the removal of portions of a bulk deposited film by polishing using damascene processing techniques. In damascene, or dual damascene processing techniques, an opening is formed within a substrate surface. A bulk film is then deposited over the surface of the substrate and within the openings. The polishing operation is used to remove the bulk of the deposited film from over the plane of the substrate surface, while maintaining the deposited material within the openings, thereby forming a planarized surface including portions of the deposited material and the substrate surface. When the deposited material is a conductive material such as metal, a wiring pattern may be formed of the conductive material which remains within the openings and forms conductive lines according to the above damascene processing techniques. FIG. 1 is a cross-sectional view showing a typical damascene structure ready for polishing. In the exemplary embodiment shown in FIG. 1, the conductive film used in damascene processing comprises a composite film formed of a bulk metal film over a barrier layer film. In other exemplary embodiments, the barrier layer film may not be needed and the bulk metal film may be formed directly over the surface and within the openings.

In FIG. 1, subjacent layer 2 includes upper surface 10 and trenches 4 which extend down from upper surface 10. Upper surface 10 is essentially planar. In an exemplary embodiment, subjacent layer 2 may be an insulating film formed over a semiconductor substrate such as a silicon wafer, or subjacent layer 2 may represent the semiconductor substrate itself. Trenches 4 may be formed within subjacent layer 2 by etching or other commonly available processing techniques. In an exemplary embodiment, the trenches may be multi-tiered trenches (not shown) such as used in dual damascene processing. The trenches 4 formed within subjacent layer 2, may alternatively be grooves or other openings such as via openings. Hereinafter, these openings will be referred to collectively as "trenches".

Barrier layer film 6 is formed within trenches 4 and over upper surface 10. Conductive material 8 is a film formed over barrier layer 6 and includes top surface 14. In various exemplary embodiments, the barrier layer film may be titanium, tantalum, tungsten, titanium nitride, titanium silicide, tantalum nitride, tantalum silicide, tungsten silicide or other refractory metals. Barrier layer film 6 may be formed using any suitable conventional method. Conductive film 8 which fills trenches 4 and is formed over top surface 12 of barrier layer film 6, will commonly be a metal such as aluminum, copper, tungsten, or their alloys, but any metal-containing film used in such a damascene application, may be polished and "endpointed" according to the present invention. During the chemical mechanical polishing operation, thickness 20 of the bulk portion of conductive film 8 is reduced. Alternatively illustrated, the uppermost surface of the substrate to be polished, is shown on grid 100 as position 114 which corresponds to top surface 14 prior to polishing.

It should be pointed out that the figures are not drawn to scale. Rather, the features have been arbitrarily expanded or reduced for clarity, as is customary. For example, the trenches, as illustrated, suggest a greater depth and width than in practice. Also, the trenches may be spaced much farther apart than as illustrated. As such, when a bulk film is formed over a surface containing trenches and also within the trenches, it should be understood that the amount of the film included within the trenches is negligible when compared to the entirety of the originally formed film.

Figure 2:
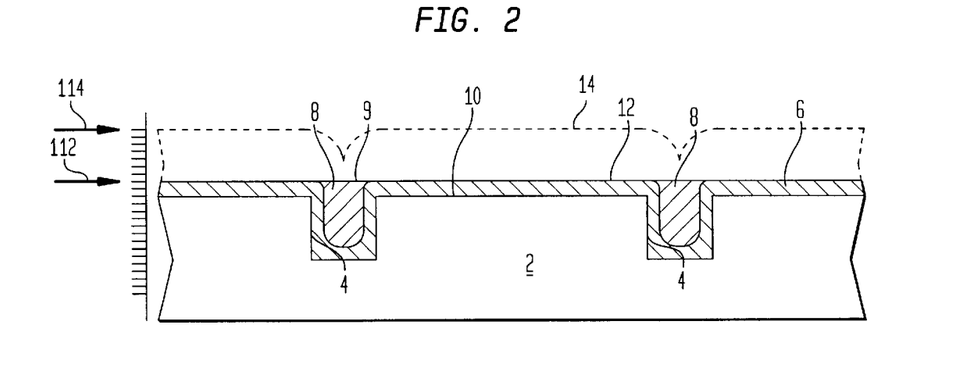
FIG. 2 is a cross-sectional view showing the structure as in FIG. 1, after the bulk of the metal film has been removed by polishing.
Figure 3:
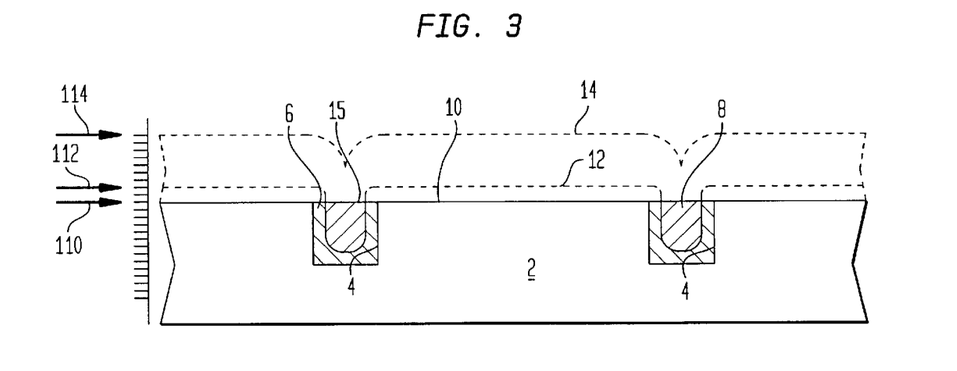
FIG. 3 is a cross-sectional view showing the structure as in FIG. 2, after the bulk of the barrier layer film has also been removed by polishing.
Figure 4:
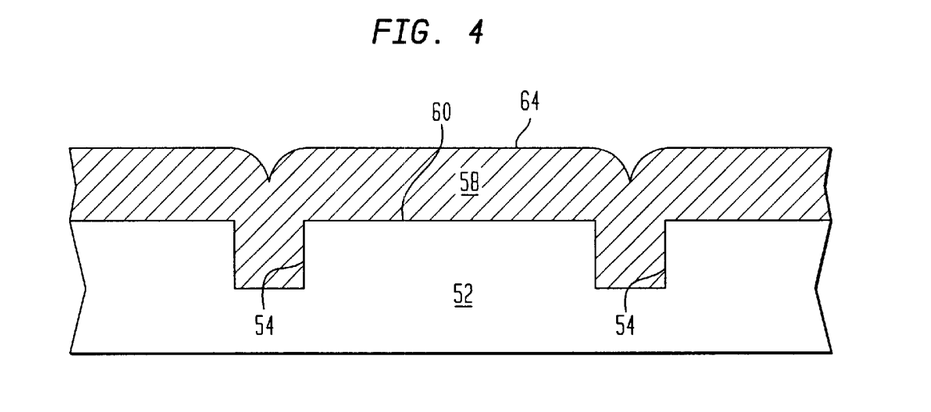
FIG. 4 is a cross-sectional view of another exemplary embodiment of a metal film structure ready for polishing.
Figure 5:
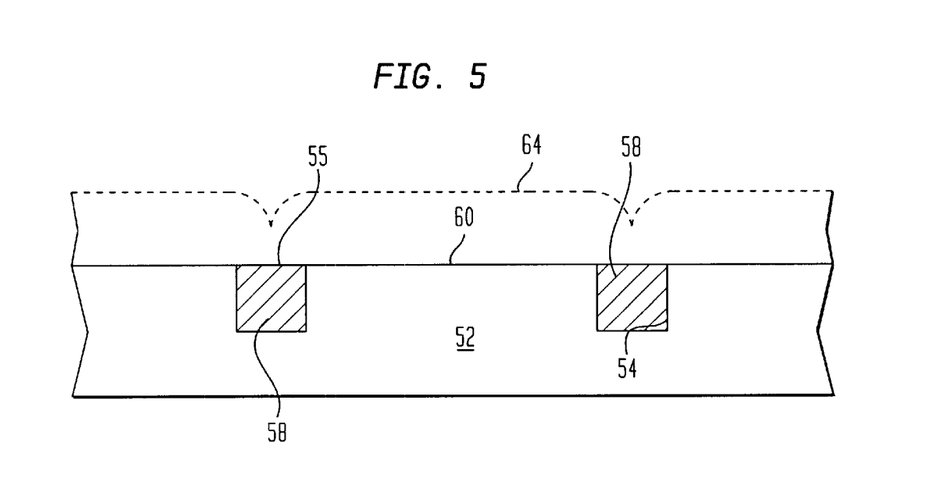
FIG. 5 is a cross-sectional view showing the structure as in FIG. 4, after the bulk of the metal film has been removed by polishing.

FIGS. 1–3 illustrate a planarization process involving the sequential removal of films using a CMP operation. FIGS. 4 and 5 show a sequence of processing steps used to remove and planarize another exemplary embodiment of a film structure. The CMP operation used to remove the films by polishing, may be any suitable CMP process such as available in the art. Any suitable CMP apparatus may be used. Likewise, the operating conditions or parameters of the CMP operation and the settings of the CMP apparatus may be chosen as suitable for the particular CMP operation being performed. Parameters may include the speed at which the polishing pad is rotated, the speed at which the substrate is rotated, the flow rate and composition of the polishing slurry being supplied to the polishing operation, the roughness of the polishing pad surface, the downward force applied to urge the substrate being polished against the polishing pad, and so forth.

As the film structure shown in FIG. 1 is subjected to a CMP operation, it can be seen that top surface 14 of conductive film 8, will be receded. Now turning to FIG. 2, it can be seen that substantially all of conductive film 8 which was formed over upper surface 10, has been removed by polishing. Conductive film 8 remains only in trenches 4, and barrier layer film 6, including top surface 12, is exposed. As such, FIG. 2 represents the "endpoint" of the polishing operation for removing the bulk portion of conductive film 8. Once again, it is stressed that the features of the trenches 4 have been expanded to show the structure formed within the trenches 4 and, as such, the trenches are shown in much closer proximity than in practice. It should be further understood that, relative to the overall surface of the substrate being polished, the surface area including the exposed surfaces 9 of the conductive film 8 which lies within trenches 4, is very small in comparison to the exposed area of upper surface 12 of exposed barrier layer film 6 and that the amount of conductive film 8, which remains in trenches 4, is negligible when compared to originally formed conductive film 8. Position 112 on grid 100 corresponds to top surface 12 and indicates that the uppermost surface of the substrate being polished, has been receded with respect to the original uppermost surface indicated by position 114 of grid 100, and the top surface 14 of originally formed conductive film 8, as indicated by the ghost pattern.

Now turning to FIG. 3, the CMP operation continues, as above, and removes barrier layer film 6 from over upper surface 10. Upper surface 10 of subjacent layer 2 is now exposed. Trenches 4 include sections of barrier layer film 6 disposed peripherally around the trench, and portions of conductive film 8. It can be seen that top surface 15 of the structure formed within the trenches 4, is substantially planar with upper surface 10 of subjacent layer 2. FIG. 3 represents the endpoint of the polishing operation used to remove barrier film 12, and therefore the second endpoint in the polishing process sequence. FIGS. 2 and 3 therefore represent the two endpoints achieved in a sequential polishing sequence used to remove two films from over substrate, while leaving portions of each of the films within a trench formed within the substrate. Position 110 on grid 100 corresponds to upper surface 10 and shows the continued recession of the uppermost surface 10 of the substrate.

FIG. 4 shows another exemplary embodiment wherein a subjacent layer 52 includes trenches 54 and upper surface 60. Conductive film 58 is a single metal-containing film which has a top surface 64, and is formed over top surface 60 and within trenches 54. A suitable CMP polishing operation may be used to remove conductive film 58 from over upper surface 60 of subjacent layer 52, and which leaves portions of conductive film 58 within trenches 54. It can be seen, in FIG. 5, that portions of conductive film 58 have been substantially removed exposing upper surface 60 of subjacent layer 52. The resulting trench structures include top surface 55 which is essentially coplanar with upper surface 60 of subjacent layer 52. FIG. 5, therefore, represents the endpoint for the polishing operation of conductive film 58, for a process where it is desired to produce a planarized substrate surface having conductive lines formed within trenches formed therein, such as in damascene processing.

It should be understood that the endpointing detection method of the present invention may be adapted to detect the endpoint condition shown in FIG. 2, FIG. 3, or FIG. 5. It should be further understood that the endpointing technique of the present invention finds much broader application in the field of CMP. For example, a bulk, metal containing film, or a stack of bulk, metal containing films may be removed by polishing, from over a substrate surface which is essentially planar. According to other exemplary embodiments, the metal containing films which are being removed by polishing, and which may be endpointed according to the process of the present invention, may be formed over substrates having various underlying features.

Figure 6:
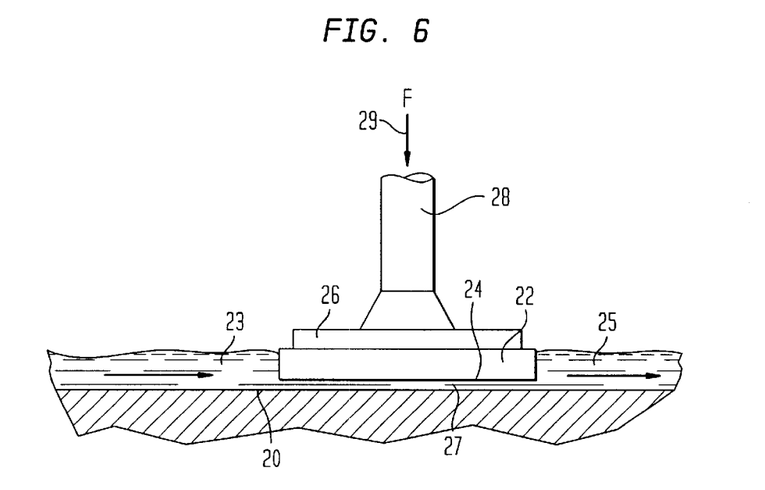
FIG. 6 is a side view of a CMP apparatus showing an effluent slurry.

FIG. 6 is a side view showing a substrate being polished using an exemplary embodiment of a CMP apparatus. Substrate 22 includes surface 24 which is being polished. Surface 24 which is being polished, may correspond to any of the substrate surfaces shown in FIGS. 1–5, during various stages of the polishing process. Substrate 22 which may be a semiconductor wafer on which integrated circuit devices are formed, as in the preferred embodiment, is held by carrier 26 which is securely attached to shaft 28. The CMP operation includes a mechanical aspect which includes a force F which urges the shaft, carrier, and substrate along direction 29 to force the substrate surface 24 against the polishing pad surface 20. In an exemplary embodiment, shaft 28 may rotate about its axis thereby rotating carrier 26 and substrate 22, thereby mechanically moving surface 24 with respect to pad surface 20. Also in the exemplary embodiment, pad surface 20 may be rotated with respect to the assembly including spindle shaft 28, carrier 26, and substrate 22. Pad surface 20 will be rotated about an axis other than the axis of shaft 28. The two relative motions provide a mechanical aspect to the chemical mechanical polishing operation.

A liquid polishing slurry inlet stream 23 is directed to interface 27 formed between polishing pad surface 20 and surface 24 of substrate 22 which is being polished. Although surface 24 substantially contacts pad surface 20 to enable polishing, interface 27 has been expanded, in the figure, to illustrate that polishing slurry is included at the interface. Effluent slurry stream 25 exits the surface being polished. It should be understood that the above description of a CMP apparatus is intended to be exemplary only. Various other CMP apparatuses which provide such an effluent slurry stream, may be used alternatively.

The polishing slurry includes abrasives which aid in the mechanical aspect of the polishing operation. The slurry may further include chemical aspects. When a metal containing film is being polished, the slurry will include an acidic component. The acid within the slurry aids in attacking and removing the metal containing material being polished, by way of chemical reaction. The slurry solution may be chosen to include any suitable acid depending on the polishing operation and the composition of the metal containing film being polished. Sulfuric acid, acetic acid, propionic acid, and phosphoric acid are examples of acids commonly included in polishing slurries. During the polishing operation, the metal within the metal containing film is oxidized by the acid according to the following equations:

$$H_2O_2 \xrightarrow{acid} O + H_2O \qquad (1)$$

$$M_{film} + O \rightarrow MO_x, \text{removed} \qquad (2)$$

It can be therefore seen that the effluent slurry stream 25 contains products of the above reactions, including oxidized metal ($MO_x$) formed from the metal in the metal containing film which is being removed by polishing. In various exemplary embodiments, metal "M" may represent aluminum, copper, tungsten, titanium, tantalum or other materials. CMP is a continuous operation, and inlet slurry stream 23 is fed continuously to the operation. Consequentially, effluent slurry stream 25 is continuously produced and may be withdrawn from the operation using conventional methods. During the polishing of a metal containing film using an acidic slurry, the continuously produced effluent slurry stream 25 will continue to contain a concentration of oxidized metal, as above.

When an endpoint condition is attained, as shown in FIGS. 2, 3, and 5, there is very little oxidized metal being produced. As such, the concentration of oxidized metal within effluent slurry stream 25 drops significantly. The present invention is directed to detecting endpoint by detecting a change in the components within the effluent slurry stream 25 as shown in FIG. 6. More specifically, the present invention is directed to detecting an endpoint condition by noting a change in the activity of the components within effluent slurry stream 25.

Figure 7:
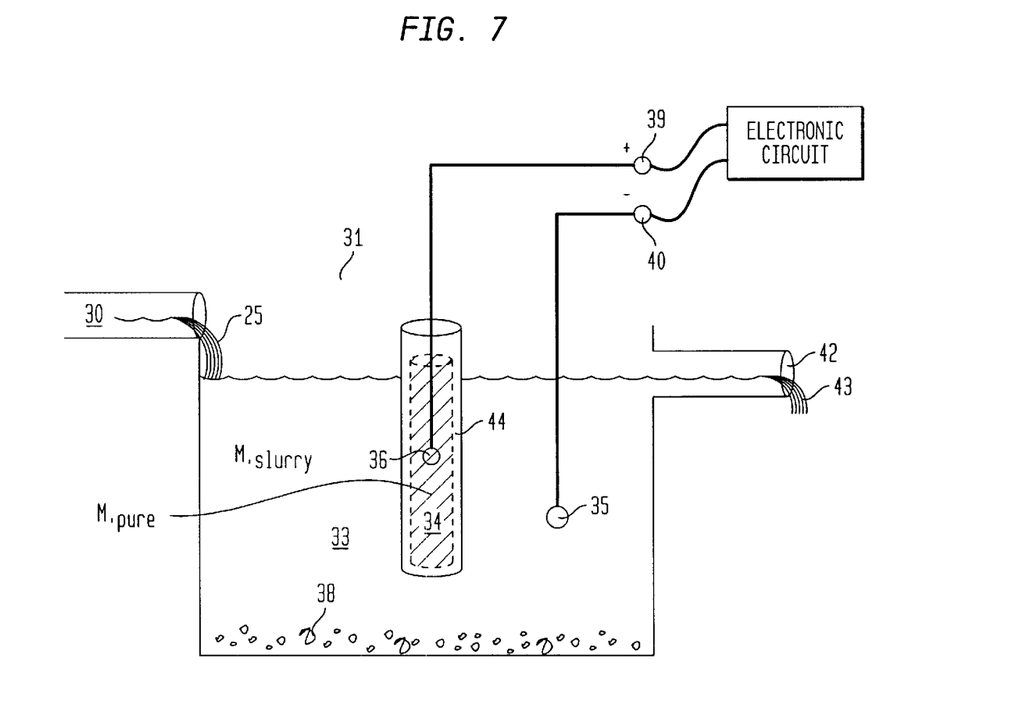
FIG. 7 is a representative view of an electrochemical cell which uses a sample of the effluent slurry as a working electrode.

A sample of effluent slurry stream 25 is withdrawn from the polishing operation, then introduced into an electrochemical cell, in which the sample of the effluent slurry stream functions as a working electrode. FIG. 7 shows effluent slurry stream 25 being delivered by way of delivery means 30 to electrochemical cell 31. The delivery of slurry stream 25 to electrochemical cell 31 may be continuous or intermittent. Electrochemical cell 31 includes a vessel 37 for retaining a sample of effluent slurry stream 25 which is provided to the electrochemical cell 31. Conventional means for withdrawing effluent slurry stream 25 from the site of the polishing operation, specifically from the interface formed between the polishing pad and the surface being polished as shown in FIG. 6, may be used to deliver a sample of effluent slurry stream 25 to electrochemical cell 31.

Electrochemical cell 31 employs a solid electrolyte 44 separating working electrode 33 from reference electrode 34 and enabling the transfer of anions across solid electrolyte 44. In the preferred embodiment, a solid yttria stabilized zirconia solution (YSZ) may be used as solid electrolyte 44. YSZ is an ideal solid electrolyte which selectively permits only $O^{-2}$ ions to diffuse through it. In an exemplary embodiment in which electrochemical cell 31 is designed to allow the half-cell reactions in the reference 34 and working 33 electrodes to involve liberation of $O^{-2}$ at one electrode compartment and the simultaneous consumption of $O^{-2}$ at the other electrode compartment, the transfer of $O^{-2}$ ions across solid YSZ electrolyte 44 occurs. This exemplary embodiment represents an oxide-type solid-state electrochemical cell.

Since the metals which are commonly used in the semiconductor manufacturing industry (W, Ti, Ta, Cu, Al) form stable metal oxides, an oxide-type solid-state electrochemical cell as above, is well suited for an endpoint detection system using electrochemical techniques.

Liquid-phase working electrode 33 consists of a sample of the effluent slurry in conjunction with a metal oxide which is used to initiate the half-cell reaction in working electrode 33 of the electrochemical cell 31. Working electrode 33 is contained within vessel 37. Metal oxide solids 38 may be added within vessel 37 of electrochemical cell 31 to serve as the metal oxide source used to initiate this reaction within the working electrode. Reference electrode 34 is a solid phase heterogeneous mixture of a pure metal, and its corresponding metal oxide. Solid phase reference electrode 34 may be in powder form. The metal included in reference electrode 34 will preferably be the same metal which is being polished and which is therefore included in effluent slurry stream 25. This ensures execution of complementary half-cell reactions in both working electrode 33 and reference electrode 34 of electrochemical cell 31. The metal oxides added to both the compartment of working electrode (solids 38), and included in reference electrode 34, do not adversely effect the working of electrochemical cell 31. The involvement of the metal oxide occurs only during the half-cell reactions; their effect is nullified during the overall cell reaction. The electrochemical cell may therefore be described as:

Working Electrode∥Electrolyte∥Reference Electrode
$M_{slurry}, MO_x \| YSZ \| M_{pure}, MO_x$ Within vessel 37, the sample of effluent slurry forms liquid-phase working electrode 33 of electrochemical cell 31. Outlet port 42 provides an outlet for liquid-phase working electrode 33. According to the illustrated embodiment, a steady state condition may be achieved after a liquid level 46 is achieved in vessel 37, at which point the amount of slurry sample being introduced by effluent slurry stream 25 equals the amount of slurry sample being removed through outlet stream 43. In this embodiment, it can be seen that liquid-phase working electrode 33 is a dynamically changing solution. In another embodiment, outlet port 42 may not be used to provide a dynamically changing effluent slurry sample, and discrete samples of effluent slurry stream 25 may be periodically introduced into electrochemical cell 31 to form working electrode 33, then dispensed. Lead wire 35 is provided within working electrode 33 to provide electrical contact to external electronic circuitry through terminal 40.

In an exemplary embodiment, the effluent slurry solution may be heated using conventional means, either as it is being delivered to the electrochemical cell, or once within the electrochemical cell. In the preferred embodiment, the effluent slurry stream may be heated to a temperature within the range of 300° C. to 400° C., but other temperatures within the range of 200° C. to 600° C. may be used alternatively.

Solid electrolyte 44 separates liquid-phase working electrode 33 from solid phase reference electrode 34, within electrochemical cell 31. According to the exemplary embodiment, reference electrode 34 is physically contained within solid electrolyte 44 which is also in contact with liquid-phase working electrode 33. In an exemplary embodiment, solid electrolyte 44 shares a contumelious surface with working electrode 33. Within reference electrode 34 is lead wire 36 which is also coupled to terminal 39 for external circuitry.

Solid electrolyte solution 44 is chosen to allow for the exchange of ions between reference electrode 34 and working electrode 33. In a preferred embodiment, solid electrolyte solution 44 is chosen to allow for the interchange of oxygen ($O^{-2}$) ions between liquid-phase working electrode 33 and solid-phase reference electrode 34. In the exemplary embodiment shown, solid electrolyte solution 34 may take on a cylindrical shape which contains reference electrode 34. It should be understood, however, that the shape of the solid electrolyte solution is not intended to be limited to the cylindrical shape shown in the exemplary embodiment.

In the preferred embodiment where the solid electrolyte 44 may be a solid solution of yttria stabilized zirconia (YSZ), the YSZ may comprise 2 to 12 weight percent of $Y_2O_3$ within $Zr_2O_3$. The solid YSZ is selective to $O^{-2}$ ions. The $O^{-2}$ ions is transferred between reference electrode 34 and liquid phase working electrode 33 as the following two half-call reactions take place within the electrochemical cell:

$$ReferenceElectrode(34) \quad M_{pure} + \frac{x}{2}O^{-2} \Rightarrow MO_x + xe^- \quad (3)$$

$$WorkingElectrode(33) \quad MO_x + xe^- \Rightarrow M_{slurry} + \frac{x}{2}O^{-2} \quad (4)$$

$$OverallCellReaction \quad M_{pure} = M_{slurry}$$

Within the electrochemical cell, the above reactions occur simultaneously, resulting in a difference in chemical potential (molar concentration) of the $O^{-2}$ ions across the electrolytes which separate the half-cells. This difference in chemical potential across the electrolytes is afforded by $O^{-2}$ ions diffusing from the oxidized metal within the slurry which forms liquid phase working electrode 33, to the metal contained within reference electrode 34.

The $O^{-2}$ ions diffuse across the electrolyte such that the generation of $O^{-2}$ in one half-cell reaction is balanced by the consumption of $O^{-2}$ ions in the corresponding half-cell reaction. This creates an excess (due to $O^{-2}$ consumption and as shown in the reference electrode 34) or scarcity (due to $O^{-2}$ generation and as shown in the working electrode 33) of electrons ($e^-$) in the corresponding electrode as each electrode tends towards electroneutrality. This results in a net positive or net negative potential developed on either of the lead wires 35 or 36. The difference in electric potential between lead wires 35 and 36 is called the open circuit potential or electromotive force (emf).

At equilibrium, the chemical potential gradient caused by the diffusion of $O^{-2}$ ions across the electrolytes, is balanced by the electric potential gradient and is indicated by a stable open circuit electromotive force (emf) across the electrolyte. This electric potential gradient can be measured across terminals 39 and 40 using conventional electronic circuitry 50, or other means. This gradient, or difference in electric potential, may be read in volts or millivolts. The electric potential difference may be read essentially continuously or periodically, at a suitable frequency.

The open circuit emf is directly related to the chemical activity of the polished component in the slurry by the Nernst equation, which governs the electric potential of the electrodes of each half-cell and may be expressed as:

$$E = E^\circ - (RT/zF) \cdot \ln K \quad (5)$$

or $$E = E^\circ - (RT/zF) \cdot \ln(a[RED]/a[OX]) \quad (6)$$

In the Nernst equation, z represents the valance of the species being reduced, F represents the Faraday constant, E represents potential of the electrode of the half-cell reaction, $E^\circ$ is the standard reversible potential of the electrode, R represents the universal Gas constant, T represents temperature, K is the equilibrium constant, a[RED] is the activity coefficient of the reduced species of the half cell reaction, and a[OX] is the activity coefficient of the oxidized species of the half cell reaction. In solution, the activity coefficients are generally taken as the molar concentrations. For the reference electrode, the activity of the metal is a[OX]=1. Thus, equation (6) simplifies as follows:

$$zF(E - E^\circ) = -RT \ln a[RED] \quad (7)$$

The quantities of the left hand side of equation (7) are known or may be measured. When the metal activity, a[RED] in the slurry changes, it will be reflected as a change in the open circuit emf ($E - E^\circ$) which may be measured using conventional means. Furthermore, the activity a[RED] of the metal species can be calculated using the measured emf.

When an endpoint condition is attained, the concentration of the oxidized metal species being produced as a result of the polishing operation and which is included within the effluent slurry, drops significantly. As the concentration of the oxidized metal species drops, so does the activity a[RED], resulting in a new equilibrium condition for the half-cell reactions and, therefore, a change in the measured open circuit emf. A conventional electronic circuit 50, or other means may be connected across terminals 39 and 40 to measure the emf across the open circuit which changes as a result of the changed composition and activity of the metal species within the effluent slurry solution.

A signal may be developed from the measured open circuit emf. Any suitable conventional method may be used to measure the open circuit emf and to display a signal of the measured value over time, either digitally, graphically or using other electronic means. As such, conventional means used to measure an electric potential gradient across terminals 39 and 40 (the open circuit emf), can be used to detect a change in the component activity within the effluent slurry stream, such as which occurs when endpoint is attained.

Reactions taken in response to the determination that endpoint condition has been attained, may be taken when a single abrupt change in the electric potential signal is detected, or in response to a steady state condition being achieved by the electric potential signal after a change. The time at which to respond to a change in the emf signal, may be determined by the polishing operation being performed, and will reflect the amount of "overetch" desired. Once a determination of endpoint has been made, the reaction taken to adjust the polishing operation may be a manual one, or it may include an electronic circuit providing a real time, feed-forward signal to automatically adjust the polishing operation. Conventional electronic circuitry available in the art may be used to provide a signal to the polishing apparatus in response to endpoint being detected.

The sampling frequency of the electrical potential measurement taken between terminals 39 and 40 will vary based on the polishing operation. For example, in the case where 10,000 angstroms of a copper film is being removed by polishing, the expected time for endpoint to be attained, may range from 2 to 6 minutes depending on the polishing conditions used. For such a polishing operation, a sampling frequency of 5 to 10 seconds may be used. In other exemplary embodiments, the sampling frequency may vary based on the film being polished, the thickness of the film being polished, and the polishing conditions. In another exemplary embodiment the electric potential difference may be measured virtually continuously.

In response to an endpoint condition being detected, the entire polishing process may be terminated, or the polishing process may be otherwise adjusted. The adjustment of the polishing process may include adjusting any of the various parameters and settings which affect the operating conditions. For example, a buffing operation may be initiated, or a further polishing operation may be commenced to polish underlying features. In any event, by accurately determining the endpoint condition, further unwanted polishing is avoided and undesired effects such as dishing within the underlying features, is prevented.

Now referring again to FIGS. 2 and 3, the first endpoint condition in the polishing process, may be attained and detected at the point of the polishing process represented by FIG. 2. At that point, the polishing process may be adjusted to produce a polishing operation directed to polishing barrier layer film 6. Likewise, a second endpoint condition in the polishing process, may be attained and detected, at the point of the polishing process represented by FIG. 3. After the removal of the bulk of barrier layer film 6 from over upper surface 10, and as indicated by a change in the electric potential measured across terminals 39 and 40 as a result of the change of concentration of polished metal species in the effluent slurry solution, a number of actions may be taken. For example, the polishing process may be adjusted and allowed to continue, the process sequence may be terminated, or a buffing operation may be initiated.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principals, aspects, and embodiments of the invention, as well as specific examples thereof, are intended to encompass both structural and functional equivalents thereof. Additionally, it is intended that such equivalents include both currently known equivalents such as equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed:

1. An endpoint detector for a chemical mechanical polishing operation, comprising an electrochemical cell including a reference electrode, a liquid-phase working electrode formed of a sample of an effluent slurry of said chemical mechanical polishing operation, a solid electrolyte contacting both of said reference electrode and said working electrode, and an electronic circuit for measuring an electronic potential difference between said reference electrode and said working electrode.

2. The endpoint detector as in claim 1, wherein said solid electrolyte includes a surface being contumelious with said working electrode, and a further surface being conterminous with said reference electrode.

3. The endpoint detector as in claim 1, wherein said solid electrolyte selectively allows for an interchange of oxygen ions between said working electrode and said reference electrode.

4. The endpoint detector as in claim 1, wherein said solid electrolyte comprises a solid yttria stabilized zirconia solution.

5. The endpoint detector as in claim 4, wherein said solid yttria stabilized zirconia solution includes $Y_2O_3$ and $Zr_2O_3$, said $Y_2O_3$ having a weight percentage within a range of 2–12%.

6. The endpoint detector as in claim 1, wherein said electronic circuit is adapted for measuring an open circuit electromotive force of an open circuit including said working electrode and said reference electrode.

7. The endpoint detector as in claim 1, wherein said electronic circuit is coupled to a metal lead disposed within said working electrode and further coupled to a further metal lead disposed within said reference electrode.

8. The endpoint detector as in claim 1, wherein said effluent slurry includes a metal oxide of a metal species being polished, and said reference electrode includes said metal species and said metal oxide.

9. The endpoint detector as in claim 1, wherein said electronic circuit is capable of providing a signal of said potential difference.

10. The endpoint detector as in claim 9, wherein said electronic circuit is capable of providing a signal to a chemical mechanical polishing apparatus responsive to a change in said electric potential difference, said chemical mechanical polishing operation being carried out within said apparatus.

11. The endpoint detector as in claim 1, wherein said electrochemical cell includes a vessel having an inlet port for receiving said sample of said effluent slurry, containing means for containing said sample, and an outlet port for allowing said sample to exit said vessel.

12. The endpoint detector as in claim 1, wherein said effluent slurry is received within said vessel substantially continuously, a portion of said sample exits said vessel substantially continuously and said sample is a dynamic sample.

13. The endpoint detector as in claim 1, wherein said electronic circuit measures said potential difference periodically.

14. The endpoint detector as in claim 1, wherein said reference electrode is a powder.

15. The endpoint detector as in claim 1, further comprising solid metal oxide particles added to a vessel which contains said working electrode.

16. The endpoint detector as in claim 1, wherein said reference electrode is contained within said solid electrolyte.

17. An endpoint detector for a chemical mechanical polishing operation comprising:

an electrochemical cell including a liquid-phase working electrode formed of a sample of an effluent slurry of said chemical mechanical polishing operation, a solid electrolyte solution having a surface conterminous with said working electrode and containing a solid reference electrode, said reference electrode including a metal and an oxide of said metal, and said effluent slurry including reaction products of said polishing operation, including said oxide; and an electronic circuit coupled to said working electrode and said reference electrode and capable of measuring a potential difference therebetween;

wherein an interchange of oxygen ions between said reference electrode and said working electrode is allowable.

18. The endpoint detector as in claim 17, wherein said solid electrolyte solution comprises a yttria stabilized zirconia solution.

19. The endpoint detector as in claim 17, wherein said electrochemical cell includes a vessel having an inlet port for receiving said sample of said effluent slurry, containing means for containing said sample, and an outlet port for allowing said sample to exit said vessel.

* * * * *